United States Patent
Coates et al.

(10) Patent No.: US 6,787,624 B2
(45) Date of Patent: Sep. 7, 2004

(54) BIS(SALICYLALDIMINATO)TITANIUM COMPLEX CATALYSTS, HIGHLY SYNDIOTACTIC POLYPROPYLENE BY A CHAIN-END CONTROL MECHANISM, BLOCK COPOLYMERS CONTAINING THIS

(75) Inventors: Geoffrey W. Coates, Ithaca, NY (US); Jun Tian, LaPorte, TX (US); Phillip D. Hustad, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/386,694

(22) Filed: Mar. 13, 2003

(65) Prior Publication Data

US 2003/0176605 A1 Sep. 18, 2003

Related U.S. Application Data

(62) Division of application No. 09/954,199, filed on Sep. 18, 2001, now Pat. No. 6,562,930.

(51) Int. Cl.$^7$ ..................... C08F 210/06; C08F 210/02; C08F 210/16
(52) U.S. Cl. .................. 526/348; 526/161; 526/348.6; 526/351
(58) Field of Search ................................ 526/348, 161

(56) References Cited

U.S. PATENT DOCUMENTS

| | | | |
|---|---|---|---|
| 5,708,101 A | 1/1998 | Bercaw et al. | 526/127 |
| 5,710,222 A | 1/1998 | Ewen et al. | 526/127 |
| 5,840,389 A * | 11/1998 | Asanuma et al. | 428/36.91 |
| 6,121,377 A | 9/2000 | Chien | 525/88 |
| 6,265,503 B1 | 7/2001 | Razavi et al. | 526/160 |
| 6,562,930 B2 | 5/2003 | Coates et al. | |
| 2002/0120080 A1 | 8/2002 | Demain | 526/170 |
| 2003/0114623 A1 * | 6/2003 | Mitani et al. | 526/352 |

FOREIGN PATENT DOCUMENTS

| | | |
|---|---|---|
| EP | 351391 | 1/1990 |
| EP | 351392 | 1/1990 |
| EP | 874005 | 10/1998 |
| WO | WO 01/55231 * | 8/2001 |

OTHER PUBLICATIONS

Saito, J., et al., Chemistry Letters 2001, pp 576–577.
Saito, J., et al., Angew. Chem. Int. Ed. 40, No. 15, 2918–2920 2001.
Tian, J., et al., Angew. Chem. Int. Ed. 39, No. 20, 3626–3629 (Oct. 16, 2000).
Tian, T., et al., J. Am. Chem. Soc. 123, 5134–5135 (May 4, 2001).
Odian, G, Principles of Polymerization, 3$^{rd}$ edition, John Wiley & Sons, New York, pp. 675–676.

* cited by examiner

Primary Examiner—Roberto Rabago

(57) ABSTRACT

Bis(salicylaldiminato)titanium complex with optionally substituted phenyl or cyclohexyl on nitrogen catalyzes highly syndiospecific polymerization of propylene. Syndiotactic polypropylene with defects of the type rmr having [rrrr] content greater than 0.70 and block copolymer containing block(s) of the syndiotactic polypropylene and block (s) of poly(ethylene-co-propylene) and/or poly(alpha-olefin-co-propylene) are obtained. Certain of the catalysts provide living polymerization. Living olefin polymers and olefin terminated oligomers and polymers are also products.

7 Claims, No Drawings

BIS(SALICYLALDIMINATO)TITANIUM COMPLEX CATALYSTS, HIGHLY SYNDIOTACTIC POLYPROPYLENE BY A CHAIN-END CONTROL MECHANISM, BLOCK COPOLYMERS CONTAINING THIS

CROSS-REFERENCE TO RELATED APPLICATIONS

This is a division of U.S. application Ser. No. 09/954,199, filed Sep. 18, 2001, now U.S. Pat. No. 6,562,930.

The invention was made at least in part with United States Government support under National Science Foundation related grant CCMR (Cornell Center for Materials Research) Giant Number DMR 0079992. The United States Government has certain rights in the invention.

TECHNICAL FIELD

This invention is directed to bis(salicylaldiato)titanium complex catalysts, and highly syndiotactic polypropylene makable therewith by a chain-end control mechanism, and block copolymers containing the syndiotactic polypropylene and poly(ethylene-co-propylene) and/or poly(alpha-olefin-co-propylene), as well as to living olefin polymers and to olefin terminated oligomers and polymers and to methods of making syndiotactic polypropylene, block copolymers and olefin-terminated oligomers and polymers from propylene.

BACKGROUND OF THE INVENTION

The kind of polypropylene in general use, for example, for packaging and container functionality, is isotactic polypropylene. It is typically described as having the methyl groups attached to the tertiary carbon atoms of successive monomeric units on the same side of a hypothetical plane through the main chain of the polymer. Isotactic polypropylene lacks clarity and thus is not useful in cases where this is important.

Another kind of polypropylene is syndiotactic polypropylene. It may be described as having the methyl groups attached to the tertiary carbon of successive monomeric units on alternate sides of a hypothetical plane through the main chain of the polymer. Syndiotactic polypropylene is clear, that is it does not have the lack of clarity characteristic of isotactic polypropylene.

There are two types of syndiotactic polypropylene. One of these types is referred to as being made by a chain-end control mechanism and contains defects of the rmr type. NMR analysis for this kind of structure is shown in Zambelli, et al., Macromolecules, 13, 267–270 (1980). The most syndiospecific polypropylene of this type made before this invention has [rrrr] pentad content of 0.63 (described in Pellecchia, C., et al., Macromol. Rapid Commun. 17, 333–338 (1996)) which limits the usage since the lower the [rrrr] pentad content, the lower the melting point. For example, a container made from polypropylene with [rrrr] pentad content of 0.63 will melt on contact with boiling water and thus is unuseful for containers for hot liquids. We turn now to the other type of syndiotactic polypropylene. It is referred to as being made by a site-control mechanism and as containing defects of the rmmr type. This type of polypropylene is described in European Patent Application Publication 0351391 A2 (published Jan. 17, 1990). Highly syndiotactic polypropylene ([rrrr]=0.97) has been made by a site-control mechanism. See Ewen, J. A., et al., J. Am. Chem. Soc., 110, 6255–6256(1988), Herzog, T. A., et al., J. Am. Chem. Soc. 118, 11988–11989 (1996), and Veghini, D., et al., J. Am. Chem. Soc. 121, 564–573 (1999). This kind of syndiotactic polypropylene has not yet been commercialized apparently because of processing and/or economic factors.

SUMMARY OF THE INVENTION

It has been discovered herein that highly syndiospecific polypropylene can be made by a chain-control mechanism by utilizing certain bis(salicylaldiminato)titanium complex compounds as catalysts as well as block copolymers containing block(s) of the syndiotactic polypropylene and block(s) of poly(ethylene-co-propylene) and/or poly(alpha-olefin-co-propylene) and that living polymerization can be obtained and that certain of the catalysts are useful in the production of olefin terminated polymers and oligomers from propylene.

The invention herein in one embodiment, denoted the first embodiment, is directed to a bis(salicylaldiminato)titanium complex having the structure:

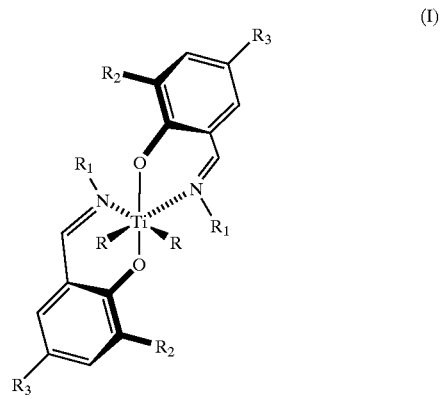

where R is selected from the group consisting of halogen atoms, $C_1$–$C_{10}$ branched or straight chain alkyl groups, $C_1$–$C_6$ branched or straight chain alkoxide groups, and $C_1$–$C_6$ branched or straight chain amido groups, $R_1$ is phenyl substituted with $C_1$–$C_6$ branched or straight chain alkyl group or electron withdrawing atom or group at the 2-position and optionally substituted with $C_1$–$C_6$ branched or straight chain alkyl groups or electron withdrawing atom or group at one or more of the 3-, 4-, 5- and 6-positions, or is $C_1$–$C_{10}$ branched, cyclic or straight chain alkyl group, and $R_2$ and $R_3$ are the same or different and are selected from the group consisting of $C_4$–$C_6$ tertiary alkyl groups; or cationic form thereof. The complexes are useful as catalysts for polymerization of olefins and are especially useful for polymerization of propylene.

The invention herein in another embodiment, denoted the second embodiment, is directed to syndiotactic polypropylene having $M_w$ ranging from 10,000 to 500,000 and defects of the type rmr and [rrrr] pentad content greater than 0.70. The syndiotactic polypropylene is useful, for example, for packaging and container functionality.

The invention herein in another embodiment, denoted the third embodiment, is directed to syndiotactic poly($C_4$–$C_6$-alpha olefins) having a $M_w$ ranging from 10,000 to 500,000 and $M_w/M_n$ ranging from 1.0 to 2.0. These syndiotactic polyolefins are useful for films and sheets because of their flexibility and transparency.

The invention herein in another embodiment, denoted the fourth embodiment, is directed to a method of preparing syndiotactic polypropylene having $M_w$ ranging from 10,000 to 500,000 and defects of the type rmr and [rrrr] pentad content greater than 0.50 comprising polymerizing propylene dissolved in an aprotic solvent in the presence of a catalytically effective amount of a complex having the structure:

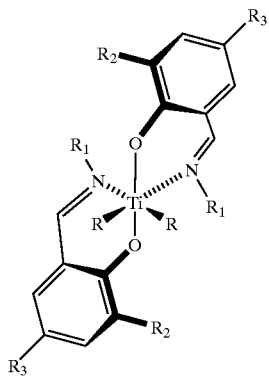
(I)

where R is selected from the group consisting of halogen atoms, $C_1$–$C_{10}$ branched or straight chain alkyl groups, $C_1$–$C_6$ branched or straight chain alkoxide groups, and $C_1$–$C_6$ branched or straight chain amido groups, $R_1$ is phenyl optionally substituted with one to five $C_1$–$C_6$ branched or straight chain alkyl groups or one to five electron withdrawing atoms or groups, or is $C_1$–$C_{10}$ branched, cyclic or straight chain alkyl group, and $R_2$ and $R_3$ are the same or different and are selected from the group consisting of H or $C_1$–$C_6$ branched or straight chain alkyl group, and an activating effective amount of compound that converts titanium of the complex to cationic form. The syndiotactic polypropylene product has packaging and container functionality.

The invention herein in still another embodiment, denoted the fifth embodiment, is directed to olefin terminated polymers and oligomers of propylene having the structure:

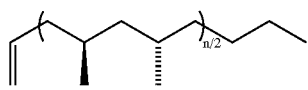
(II)

where n ranges from 1 to 750. These compounds are useful, for example, to add as so-called 'macromonomers' to other polymerizations and can be incorporated about as well as hexene.

The invention in another embodiment denoted the sixth embodiment is directed to a method of preparing polymers and oligomers of propylene having the structure (II) where n ranges from 1 to 750 comprising polymerizing propylene in an aprotic solvent in the presence of a catalytically effective amount of complex having the structure (I) where R is selected from the group consisting of halogen atoms, $C_1$–$C_{10}$ branched or straight chain alkyl groups, $C_1$–$C_6$ branched or straight chain alkoxide groups, and $C_1$–$C_6$ branched or straight chain amido groups, $R_1$ is phenyl optionally substituted at one or more of the 3-, 4-, and 5-positions but not at the 2- and 6-positions, the optional substitution at one or more of the 3-, 4- and 5-positions being with $C_1$–$C_6$ branched or straight chain alkyl group or electron withdrawing atom or group, and $R_2$ and $R_3$ are the same or different and are selected from the group consisting of H and $C_1$–$C_6$ branched or straight chain alkyl groups and an activating effective amount of compound that converts titanium of the complex to cationic form, and quenching the reaction when olefin-terminated polymer or oligomer of desired number of monomer units is formed.

The invention herein in still another embodiment, denoted the seventh embodiment, is directed to block copolymer having $M_w$ ranging from 10,000 to 500,000 comprising at least one block of syndiotactic polypropylene and at least one block of poly(ethylene/propylene) where the ethylene content ranges from 1 to 100% by weight, containing a volume fraction of syndiotactic polypropylene ranging from 0.20 to 0.99. Species include block copolymer consisting essentially of one block of syndiotactic polypropylene and one block of poly(ethylene-co-propylene), block copolymer consisting essentially of a block of syndiotactic polypropylene followed by a block of poly(ethylene-co-propylene) followed by a block of syndiotactic polypropylene, and block copolymer consisting essentially of a block of syndiotactic polypropylene followed by a block of poly(ethylene-co-propylene) followed by a block of syndiotactic polypropylene followed by a block of poly(ethylene-co-propylene) followed by a block of syndiotactic polypropylene.

The invention in still another embodiment, denoted the eighth embodiment is directed to block copolymer having $M_w$ ranging from 10,000 to 500,000 comprising at least one block of syndiotactic polypropylene and at least one block of poly(alpha-olefin/propylene), e.g., poly($C_4$–$C_6$ alpha-olefin/propylene), e.g., poly(1-butene/propylene) where the alpha-olefin content (not propylene) ranges from 1 to 100% by weight, containing a volume fraction of syndiotactic polypropylene ranging from 0.20 to 0.99.

Chain-end control and defects of the type rmr as referred to herein are described in Coates, G. W., Chem. Rev. 100, 1223–1252 (2000).

The [rrrr] pentad contents described herein are measured as described in Resconi, L., et al., Chem. Rev. 100, 1253–1345 (2000).

The term "electron withdrawing atom or group" is used herein to mean atom or group where the connecting atom of the atom or group is more electronegative than hydrogen.

The term "$M_w$" is used herein to mean weight average molecular weight, and the term "$M_n$" is used herein to mean number average molecular weight and these are determined using gel permeation chromatography (GPC) in 1,2,4-trichlorobenzene at 140° C. versus polystyrene standards, unless otherwise stated.

DETAILED DESCRIPTION

We turn now to the first embodiment of the invention which is directed to a bis(salicylaldiminato)titanium complex having the structure:

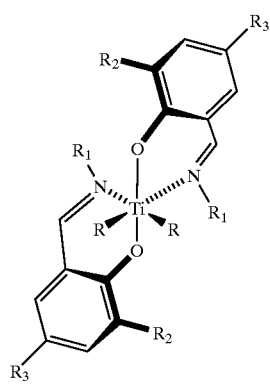

(I)

where R is selected from the group consisting of halogen atoms, $C_1$–$C_{10}$ branched or straight chain alkyl groups, $C_1$–$C_6$ branched or straight chain alkoxide groups and $C_1$–$C_6$ branched or straight chain amido groups, $R_1$ is phenyl substituted with $C_1$–$C_6$ branched or straight chain alkyl group or electron withdrawing group at the 2-position and optionally substituted with $C_1$–$C_6$ branched or straight chain alkyl group or electron withdrawing atom or group at one or more of the 3-, 4-, 5- and 6-positions, or is $C_1$–$C_{10}$ branched, cyclic or straight chain alkyl group, and $R_2$ and $R_3$ are the same or different and are selected from the group consisting of $C_4$–$C_6$ tertiary alkyl groups; or cationic form thereof.

R is described in conjunction with formula (I) as being selected from the group consisting of halogen atoms, $C_1$–$C_{10}$ branched or straight chain alkyl groups and $C_1$–$C_6$ branched or straight chain alkoxide groups and $C_1$–$C_6$ branched or straight chain amido groups. The halogen atoms include, for example, chlorine, fluorine and bromine atoms. The $C_1$–$C_6$ branched or straight chain alkyl groups include, for example t-butyl groups. In the compounds synthesized in the working examples, R is a chlorine atom.

$R_1$ is described in conjunction with formula (I) as being phenyl substituted with $C_1$–$C_6$ branched or straight chain alkyl group or electron withdrawing atom or group at the 2-position and optionally substituted with $C_1$–$C_6$ branched or straight chain alkyl group or electron withdrawing atom or group at one or more of the 3-, 4-, 5- and 6-positions, or is $C_1$–$C_{10}$ branched, cyclic or straight chain alkyl group. The $C_1$–$C_6$ branched or straight chain alkyl groups include, for example, t-butyl. The electron withdrawing groups include, for example, fluorine atoms, nitro groups, trifluoromethyl groups, cyanide groups, and aldehyde groups. In Example X hereinafter, compounds of the formula (I) with $R_1$ being phenyl substituted at least at the 2-position with fluoro were found to catalyze living polymerization of propylene as shown by $M_w/M_n$ in the range of 1.0 to 1.35, and compounds of the formula (I) with $R_1$ being phenyl substituted with fluoro at least at the 2- and 6-positions were found to catalyze polymerization of propylene to give syndiotactic polypropylene with $M_w/M_n$ in the range of 1.0 to 1.35 and defects of the type rmr and [rrrr] pentad content greater than 0.70. In Example X, compound of the formula (I) with $R_1$ being phenyl substituted with fluoro at the 2-, 3-, 4-, 5- and 6-positions, was found to catalyze polymerization of propylene to give syndiotactic polypropylene with $M_w/M_n$ in the range of 1.0 to 1.35, i.e., living polymerization, and defects of the type rmr and [rrrr] pentad content of at least 0.95.

$R_2$ and $R_3$ are described in conjunction with formula (I) as being the same or different and as being selected from the group consisting of $C_4$–$C_6$ tertiary alkyl groups. $R_2$ and $R_3$ being $C_4$–$C_6$ tertiary alkyl group was found to be advantageous in respect to catalyzing polymerization of propylene to give syndiotactic polypropylene compared to where one of $R_2$ and $R_3$ is H in providing higher activity and higher $M_n$ as indicated by a comparison of results for A and H in Table II of Example X hereinafter.

In several cases represented herein, the complexes have C-2 symmetry, i.e., both Rs are the same, both $R_1$s are the same, both $R_2$s are the same, and both $R_3$s are the same.

Cationic form of the complex is referred to. This is the form active to catalyze polymerization. As indicated later, the complex can be converted to cationic form by co-catalyst that converts titanium of the complex to cationic form, e.g., when R is chlorine, an aluminum-containing co-catalyst can be used to pull off both chlorines and convert one to methyl or where R is alkyl, the co-catalyst [$Ph_3$ C][B($C_6F_5$)$_4$] can be used to abstract one alkyl.

Complexes of the formula (I) synthesized in the working examples have the structural formula:

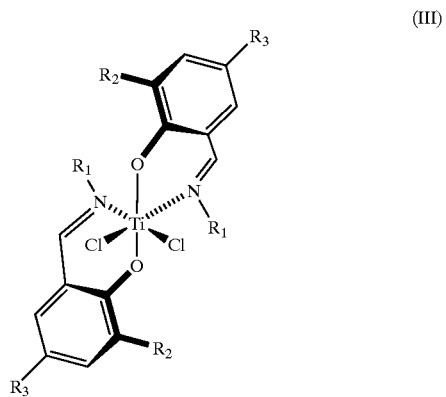

(III)

where $R_1$, $R_2$ and $R_3$ are defined as in Table 1 below:

TABLE I

| Complex | $R_1$ | $R_2$ | $R_3$ |
|---|---|---|---|
| A | Ph | $^tBu$ | $^tBu$ |
| B | (4-$^tBu$)Ph | $^tBu$ | $^tBu$ |
| C | $^cC_6H_{11}$ | $^tBu$ | $^tBu$ |
| D | (2-F)Ph | $^tBu$ | $^tBu$ |
| E | (2,6-$F_2$)Ph | $^tBu$ | $^tBu$ |
| F | (2,4,6-$F_3$)Ph | $^tBu$ | $^tBu$ |
| G | (2,3,4,5,6-$F_5$)Ph | $^tBu$ | $^tBu$ |
| H | (3,5-$F_2$)Ph | $^tBu$ | $^tBu$ |
| I | Ph | $^tBu$ | H |

In Table 1, $^cC_6H_{11}$ means cyclohexyl.

Complexes D, E, F and G of Table I are embraced by the first embodiment of the invention herein and complexes A, B, C, H and I are not embraced by the first embodiment of the invention herein.

The complexes of the formula (I) can be synthesized by reaction of 3-$R_2$, 5-$R_3$-salicylaldehyde, e.g., 3,5-di-tert-butylsalicylaldehyde where $R_2$ and $R_3$ are to be t-butyl and 3-tert-butylsalicylaldehyde where $R_2$ is to be t-butyl and $R_3$ is to be H, with aniline or substituted aniline or cyclohexylamine where the substituents provide the substituents on phenyl of $R_1$, e.g., 2-fluoroaniline where $R_1$ is to be 2-fluorophenyl, to obtain a ligand, and reacting the ligand with Ti(R)$_4$, e.g., Ti(Cl)$_4$ where R is to be Cl, in the presence of n-butyllithium and then isolating by crystallization. Where three or more fluorine substituents are on aniline reactant, the aniline reactant needs to be activated by forming the N-sulfinyl derivative of the fluoroaniline which is then reacted with the 3-$R_2$, 5-$R_3$-salicylaldehyde, e.g., N-sulfinyl-2,4,6-trifluoroaniline is used to obtain $R_1$ which is 2,4,6-trifluorophenyl. The N-sulfinyl derivative is formed by refluxing the fluoroaniline with thionyl chloride. Specific reactions are set forth in working examples I, II, III, IV, V, VI, VII, VII and IX, later herein.

In the above description of the first embodiment of the invention, compounds of the formula (I) are said to catalyze living polymerization of propylene. This means that the more of the monomer that is present, the longer the polymer obtained. The polymerization continues in this fashion until reactant is used up or the reaction is quenched by knocking the metal of the catalyst from the end of the polymer. The obtaining of living polymerization is shown by a low $M_w/M_n$, e.g., $M_w/M_n$ ranging from 1.0 to 1.35. Living polymerization provides syndiotactic polypropylene without olefin end group.

We turn now to the second embodiment of the invention, which is directed to syndiotactic polypropylene having $M_w$ ranging from 10,000 to 500,000 and defects of the type rmr and [rrrr] pentad content greater than 0.70. The polymer is made by a chain-end control mechanism since defects of the type rmr are recited. In one subgroup, the syndiotactic polypropylene has [rrrr] pentad content of at least 0.95. In another subgroup which can be overlapping with the first subgroup, $M_w/M_n$ ranges from 1.05 to 1.35 and in products made in working examples ranges from 1.06 to 1.34. The syndiotactic polypropylene of this embodiment is made by the method of the fourth embodiment described below except that complex D of Table 1 is excluded as the catalyst. Details of synthesis are presented in working Example X which is set forth later. It is noted that some publications refer to [r] instead of [rrrr] pentad content; [r] to the fourth power gives [rrrr] pentad content for chain-end control statistics. Synthesis of the syndiotactic polypropylene of this embodiment can be carried out by the method of the fourth embodiment herein as described in conjunction with catalysis by complexes providing [rrrr] pentad content greater than 0.70.

We turn now to the third embodiment, which is directed to syndiotactic poly($C_4$–$C_6$-alpha-olefins) having a $M_w$ ranging from 10,000 to 500,000 and $M_w/M_n$ ranging from 1.0 to 2.0, e.g., 1.0 to 1.5. The polymers are made by a chain-end control mechanism when defects of the type rmr are present. The alpha-olefins which are polymerized to prepare the syndiotactic poly($C_4$–$C_6$-alpha-olefins) of this embodiment include, for example, 1-butene, 1-pentene, 1-hexene, and 4-methyl-1-pentene. These polymers can be prepared by polymerizing the alpha-olefin in an aprotic solvent, e.g., toluene or hexanes, in the presence of catalytically effective amount of complex of formula (I) where R is chlorine, $R_1$ is phenyl substituted with fluoro at least at the 2- and 6-positions and $R_2$ and $R_3$ are t-butyl and an activating effective amount of compound that converts titanium of the complex to cationic form as described in conjunction with the fourth embodiment, preferably an aluminum-containing compound that converts titanium of the complex to cationic form. The polymerization is appropriately carried out at 0° C. Aluminum-containing activator compounds include, for example, methyl aluminoxane (MAO) and polymethyl aluminoxane (PMAO) (which is more soluble than methyl aluminoxane in the aprotic solvent and thus more readily stays in solution). The amount of complex of formula (I) ranges from 0.2 to 20 mmol per 1,000 µl of solution of olefin on an olefin saturated solution basis. The aluminum-containing compound activator is used in a [Al]/[Ti] (the Ti being the Ti in the complex of formula (I)) ratio ranging from 10 to 1,000.

We turn now to the fourth embodiment of the invention, which is directed to a method of preparing syndiotactic polypropylene having a $M_w$ ranging from 10,000 to 500,000 and defects of the type rmr and [rrrr] pentad content greater than 0.50 comprising polymerizing propylene dissolved in an aprotic solvent (preferably as a saturated solution) in the presence of a catalytically effective amount of complex:

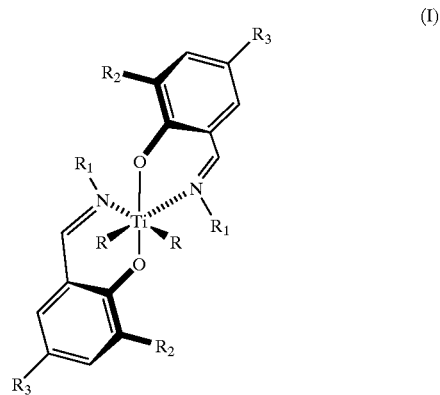

(I)

where R is selected from the group consisting of halogen atoms, $C_1$–$C_{10}$ branched or straight chain alkyl groups, $C_1$–$C_6$ branched or straight chain alkoxide groups, and $C_1$–$C_6$ branched or straight chain amido groups, $R_1$ is phenyl optionally substituted with one to five $C_1$–$C_6$ branched or straight chain alkyl groups or one to five electron withdrawing atoms or groups, or is $C_1$–$C_{10}$ branched, cyclic or straight chain alkyl group, and $R_2$ and $R_3$ are the same or different and are selected from the group consisting of H or $C_1$–$C_6$ branched or straight chain alkyl groups, and an activating effective amount of compound that converts titanium of the complex to cationic form. The aprotic solvent can be, for example, toluene or hexanes, and is preferably toluene. The complex can be prepared as described above and is used in an amount from 0.2 to 20 mmol per 1,000 ml of solution of olefin (on an olefin saturated solution basis). The compound that converts titanium of the complex to cationic form is, for example, an aluminum-containing compound. When the complex used is one where both Rs are chlorine, the aluminum-containing compound functions by pulling both chlorines from the complex and converting one to methyl. Another compound that converts titanium of the complex to cationic form is $[Ph_3C][B(C_6 F_5)]_4$; when complex is used where both Rs are alkyl, this co-catalyst abstracts one alkyl. A class of compounds that converts titanium of the complex to cationic form are clays. An aluminum-containing compound for use to convert titanium of the complex to cationic form preferably is methyl aluminoxane (MAO), very preferably polymethyl aluminoxane (PMAO) which is available from Akzo Nobel. The amount of aluminum-containing compound used ranges from 10 to 1,000 on a [Al]/[Ti] basis. Reaction temperature can range, for example, from –20 to 100° C. and is preferably 0° C. and reaction times can range, e.g., from 1 hour to 50 hours. Syndiotactic polypropylene with [rrrr] pentad content greater than 0.70 is obtained using complex of formula (I) as described above in conjunction with this embodiment, except for complex D of Table I. Syndiotactic polypropylene with $M_w/M_n$ in the range of 1.0 to 1.35 and living polymerization are obtained using complex of formula (I) as described above in conjunction with this embodiment where $R_1$ is phenyl substituted at least at the 2-position with fluorine. The reaction can be carried out, for example, at 01 to 300 psi and is carried out at 40 psi at 0° C. in Example X hereinafter. In living or other polymerization, the polymerization can be ended when desired by knocking the metal of the catalyst off the end of the product, e.g., by quenching by injection of methanol/HCl (10% by volume HCl) in amount of from 1 to 10 volume percent of the polymerization solution.

We turn now to the fifth embodiment of the invention, which is directed to olefin terminated polymers and oligomers of propylene having the structure:

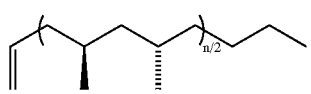

(II)

where n ranges from 1 to 750. In the formula (II), n is the number of propylene units in the polymer or oligomer except for the olefin terminating end groups. Specific examples of this embodiment have the formula (II), where n=1, 2, 3, 4, 10, 20, 50 or 100. These polymers and oligomers are prepared by a method comprising polymerizing propylene in a method which does not give living polymerization, e.g., in the method of the sixth embodiment of the invention described below.

We turn now to the sixth embodiment of the invention which is directed to a method of preparing polymers and oligomers of propylene having the structure (II) where n ranges from 1 to 750 comprising polymerizing propylene in an aprotic solvent, preferably as a saturated solution, in the presence of a catalytically effective amount of complex having the structure (I) where R is selected from the group consisting of halogen atoms, $C_1$–$C_{10}$ branched or straight chain alkyl groups, $C_1$–$C_6$ branched or straight chain alkoxide groups, and $C_1$–$C_6$ branched or straight chain amido groups, $R_1$ is phenyl optionally substituted at one or more of the 3-, 4-, and 5-positions but not at the 2- and 6-positions, the optional substitution at one or more of the 3-, 4- and 5-positions being with $C_1$–$C_6$ branched or straight chain alkyl group or electron withdrawing atom or group, and $R_2$ and $R_3$ are the same or different and are selected from the group consisting of H and $C_1$–$C_6$ branched or straight chain alkyl groups and an activating effective amount of compound that converts titanium of the complex to cationic form, and quenching the reaction when olefin-terminated polymer or oligomer of desired number of monomer units is formed.

The aprotic solvent can be, for example, toluene or hexanes and preferably is toluene. The complex and synthesis thereof is described above. Suitable complexes for use in this embodiment include complexes A, H and I of Table I above. The amount of said complex which is a catalytically effective amount ranges from 0.2 to 20 mmol per 1,000 ml of solution of propylene (on a propylene saturated solution basis). The compound that converts titanium of the complex to cationic form is the same as that described above in conjunction with the fourth embodiment of the invention herein. When the compound that converts titanium of the complex to cationic form is an aluminum-containing complex, it is preferably MAO, very preferably PMAO, used in an activating effective amount, for example, from 10 to 1,000 on a [Al/Ti] basis. Reaction temperature can range, for example, from –20 to 100° C. and preferably is 0° C., and reaction time can range, for example, from 1 hour to 50 hours. The reaction is quenched when desired amount of polymer is formed, e.g., by weighing solids in a sample and extrapolating to the whole reaction.

We turn now to the seventh embodiment of the invention, which is directed to block copolymer having $M_w$ ranging from 10,000 to 500,000 comprising at least one block of syndiotactic polypropylene and one block of poly(ethylene/propylene) where the ethylene content ranges from 1 to 100% by weight, containing a volume fraction of syndiotactic polypropylene ranging from 0.20 to 0.99. The syndiotactic polypropylene is sometimes denoted SPP hereinafter. The poly(ethylene/propylene) is polyethylene, sometimes denoted PE hereinafter, when the ethylene content of the poly(ethylene/propylene) is 100% and otherwise is poly(ethylene-co-propylene), sometimes denoted EP hereinafter. In general, the block polymers can be made by the methods for making syndiotactic polypropylene described hereinbefore but with sequential addition of monomers. The blocks of syndiotactic polypropylene preferably have [rrrr] pentad content greater than 0.70.

In one species of the seventh embodiment, there is provided a block copolymer having $M_w$ ranging from 10,000 to 500,000 consisting essentially of one block of syndiotactic polypropylene and one block of poly(ethylene-co-propylene) where the volume fraction of syndiotactic polypropylene ranges from 0.20 to 0.99. This block copolymer may be referred to as a diblock. This block copolymer can be made as follows: The method for fourth embodiment is used initially where the complex used as catalyst is one that gives living polymerization, e.g., complexes B, C, D, E, F and G in Table I. In the reaction, the aprotic solvent is preferably saturated with propylene gas under a pressure ranging from 1 to 200, e.g., 40 psi. After the initial reaction whereby syndiotactic polypropylene is produced, ethylene at an overpressure of 1 to 10 psi compared to residual propylene pressure, is introduced and reaction proceeds to add a block of poly(ethylene-co-propylene). After a desired diblock is obtained, the reaction may be quenched, e.g., by injection of methanol/10 volume percent HCl, and product is recovered by precipitation and purification. Diblock of this type is made in Example X hereafter and is the 16th entry in Table II of Example X. The volume fraction of SPP in the diblock obtained in Example X was 0.26.

In a second species of the seventh embodiment, there is provided a block copolymer having a $M_w$ ranging from 10,000 to 500,000 consisting essentially of a block of syndiotactic polypropylene followed by a block of poly (ethylene-co-propylene) followed by a block of syndiotactic polypropylene, where the volume fraction of syndiotactic polypropylene ranges from 0.20 to 0.99. This block copolymer may be referred to as a triblock. This block copolymer can be made the same as the diblock as described in the paragraph directly above, except that after the desired amount of formation of block of poly(ethylene-co-propylene), the ethylene feed is discontinued and the reaction consumes residual ethylene whereupon there is reversion to polymerization of propylene for the final block. Triblock of this type is made in Example X in three runs as indicated by the seventeenth, eighteenth and nineteenth entries in Table II of Example X. The volume fraction of SPP in the triblock of the seventeenth entry of Table II was 0.81 which gives a stiff characteristic. The volume fractions of SPP in the triblocks of the eighteenth and nineteenth entries of Table II were respectively 0.31 and 0.30 which provides an elastomeric regime since the EP block dominates.

In a third species of the seventh embodiment, there is provided a block copolymer having a $M_w$ ranging from 10,000 to 500,000 consisting essentially of a block of syndiotactic polypropylene followed by a block of poly(ethylene-co-propylene) followed by a block of syndiotactic polypropylene followed by a block of poly(ethylene-co-propylene) followed by a block of syndiotactic polypropylene, where the volume fraction of syndiotactic polypropylene ranges from 0.20 to 0.99. This block copolymer may be referred to as a pentablock. This block copolymer can be made the same as the triblock as described in the paragraph directly above, except that the propylene polymerization is interrupted twice by the addition of ethylene.

The block copolymers containing polyethylene block(s) can be made the same as the block copolymers containing block(s) of poly(ethylene-co-propylene) as described above, except for the ethylene being introduced at higher pressure if propylene is present, e.g., 200 psi, so PE blocks are formed instead of EP blocks. Alternatively, the propylene can be allowed to be consumed and the ethylene introduced at low pressure, e.g., 5 psi. Structures made in this way include SPP-EP-PE triblock, SPP-EP-PE-EP-SPP pentablock, PE-EP-SPP-EP-PE pentablock, and PE-EP-PE triblock.

We turn now to the eighth embodiment of the invention herein which is directed to block copolymer having $M_w$ ranging from 10,000 to 500,000 comprising at least one block of syndiotactic polypropylene and at least one block of poly(alpha-olefin/propylene), e.g., poly($C_4$–$C_6$ alpha-olefin/propylene), e.g., poly(1-butene/propylene), where the alpha-olefin content (not propylene) ranges from 1 to 100% by weight, containing a volume fraction of syndiotactic polypropylene ranging from 0.20 to 0.99. The term alpha-olefin is used in the description of this embodiment to mean alpha-olefin different from propylene and is preferably $C_4$–$C_6$-alpha-olefin and includes 1-butene, 1-pentene, 1-hexene, and 4-methyl-1-pentene. In general, the block copolymers can be made by the methods for making syndiotactic polypropylene described hereinbefore but with sequential addition of monomers, i.e., analogous to the way block copolymers of SPP and EP are made.

The invention is illustrated in and/or syntheses of catalysts for use in preparing embodiments of the invention are illustrated in the following working examples.

EXAMPLE I

Synthesis of Complex A

To a 250 mL Schlenk tube, 20 mL of methanol, 1.860 g (20 mmol) aniline and 4.687 g (20 mmol) 3,5-di-tert-butylsalicylaldehyde were introduced, and then heated up to reflux for 8 h. Upon reducing the solvent volume and cooling down afforded a bright brown crystals of Ligand A, which was isolated and dried under vacuum (5.882 g, 95%). $^1$H-NMR spectrum showed that it was the desired product. $^1$H NMR (CDCl$_3$, ppm, 20° C.): δ 1.32 (s, C(CH$_3$)$_3$, 9H), 1.47 (s, C(CH$_3$)$_3$ 9H), 7.18–7.30 (m, Ar, 4H), 7.36–7.46 (m, Ar, 3H), 8.63 (s, CH, 1H). Ligand A (0.718 g, 2 mmol) was dissolved in 20 mL Et$_2$O in a pre-dried Schlenk tube under nitrogen. At −60° C., the ligand solution was treated dropwise by nBuLi (1.26 mL, 1.6 M in hexanes) via gas-tight syringe. After the temperature naturally rose to room temperature, the stirring was continued for another 4 h. TiCl$_4$ (1.0 mmol, 0.1898 g) in 15 mL Et$_2$O and 4 mL toluene in another Schlenk tube was cooled down to −60° C. under nitrogen, into which the lithium salt solution of the ligand was dropwise cannulated in. After completion of the addition, stirring was continued while naturally increasing to room temperature. The reaction was further stirred for another 16 h before it was filtered through Celite under nitrogen. The volatile was removed under vacuum, obtaining a deep red fine powder, which was purified via recrystallization in benzene/hexanes at −20° C., affording red plate crystals of complex A (0.672 g, 92%). In solution, two diastereomers were present, with a $C_2$-symmetric species predominating over a $C_1$-symmetric isomer. $^1$H NMR (C$_6$D$_6$): δ 1.15 (s, C(CH$_3$)$_3$), 1.20 (s, C(CH$_3$)$_3$), 1.42 (s, C(CH$_3$)$_3$), 1.60 (s, C(CH$_3$)$_3$), 1.83 (s, C(CH$_3$)$_3$), 6.52–6.89 (m, Ar), 6.90–7.15 (m, Ar), 7.43 (s, Ar), 7.48–7.76 (m, Ar). Crystal data (solid state structure): orthorhombic, a=16.2388(13) Å, b=16.7857(13) Å, c=18.0213(14) Å, α=β=γ=90°, V=4912.2(7) Å$^3$, space group p2$_1$2$_1$2$_1$; Z=4, formula weight=891.87 for $C_{54}H_{64}Cl_2N_2O_2Ti$ and density (calc.)=1.206 g/cm$^3$; R(F)=0.033 and R$_w$(F)=0.083 (I>2σ(I))

EXAMPLE II

Synthesis of Complex B

To a 250-mL Schlenk tube were added 20 mL of methanol, 2.3434 g (10 mmol) of 3,5-di-tert-butylsalicylaldehyde, and 1.4924 g (10 mmol) of 4-tert-butylaniline. The solution was heated under reflux for 10 hours, followed by reduction of the solvent volume under vacuum. Crystallization at −20° C. afforded pale yellow crystals of Ligand B (2.81 g, 77%). $^1$H NMR, (CDCl$_3$): δ 1.35 (s, C(CH$_3$)$_3$), 1.37 (s, C(CH$_3$)$_3$), 1.48 (s, C(CH$_3$)$_3$), 7.20–7.25 (m, Ar), 7.40–7.47 (m, Ar), 8.65 (s, CH). In a Schlenk tube under nitrogen, 1.462 g (4 mmol) of Ligand B was dissolved in 20 mL of diethyl ether. The solution was cooled to −60° C. and 2.5 mL (4 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.219 mL, 2 mmol) in ether (15 mL) and toluene (4 mL) at −60° C. The reaction mixture was stirred at room temperature for 16 hours and the solvent was removed under vacuum. Residues were redisolved in methylene chloride and filtered through Celite. The solvent was removed once again, and the crude product was recrystallized in benzene/hexanes at −20° C. Red-brown crystals of Complex B were obtained (1.28 g, 70%). In solution, two diastereomers were present, with a $C_2$-symmetric species predominating over a $C_1$-symmetric isomer. $^1$H NMR (CDCl$_3$): δ 1.11 (s, C(CH$_3$)$_3$), 1.23 (s, C(CH$_3$)$_3$), 1.26–1.30 (m, C(CH$_3$)$_3$), $C_1$ isomer), 1.34 (s, C(CH$_3$)$_3$), 6.95–7.10 (m, Ar), 7.12–7.20 (m, Ar, $C_1$ isomer), 7.34 (s, Ar), 7.40 (d, Ar), 8.04 (s, CH).

EXAMPLE III

Synthesis of Complex C

To a 250-mL Schlenk tube were added 20 mL of methanol, 2.3434 g (10 mmol) of 3,5-di-tert-butylsalicylaldehyde, and 0.099 g (10 mmol) of cyclohexylamine. The solution was heated under reflux for 10 hours, followed by reduction of the solvent volume under vacuum. Crystallization at −20° C. afforded bright yellow crystals of Ligand C (2.65 g, 84%). $^1$H NMR (CDCl$_3$): δ 1.31 (s, C(CH$_3$)$_3$), 1.32–1.40 (m, Cy), 1.44 (s, C(CH$_3$)$_3$), 1.50–1.90 (m, Cy), 3.20 (m, Cy), 7.15 (d, Ar), 7.37 (d, Ar), 8.38 (s, CH). In a Schlenk tube under nitrogen, 1.262 g (4 mmol) of Ligand C was dissolved in 20 mL of diethyl ether. The solution was cooled to −60° C. and 2.5 mL (4 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.219 mL, 2 mmol) in ether (15 mL) and toluene (4 mL) at −60° C. The reaction mixture was stirred at room temperature for 16 hours and the solvent was removed under vacuum. Residues were redisolved in methylene chloride and filtered through Celite. The solvent was removed once again, and the crude product was recrystallized in methylene chloride/hexanes at −20° C. Red-brown crystals of Complex C were obtained (0.60 g, 79%). In solution, two diastereomers were present, with a C$_2$-symmetric species predominating over a C$_1$-symmetric isomer. $^1$H NMR (CDCl$_3$): δ 1.11–1.20 (m, Cy), 1.30 (s, C(CH$_3$)$_3$), 1.43–1.54 (m, Cy), 3.90 (m, Cy), 7.12 (d, Ar), 7.14 (d, Ar, C1 isomer), 7.42 (d, Ar, C$_1$ isomer), 7.53 (d, Ar, C$_1$ isomer), 7.58 (d, Ar), 8.12 (s, CH), 8.54 (s, CH, C$_1$ isomer).

EXAMPLE IV

Synthesis of Complex D

To a 250-mL Schlenk tube were added 20 mL of methanol, 1.492 g (6.36 mmol) of 3,5-di-tert-butylsalicylaldehyde, and 0.708 g (6.36 mmol) of 2-fluoroaniline. The solution was heated under reflux for 10 hours, followed by reduction of the solvent volume under vacuum. Crystallization at −20° C. afforded orange crystals of Ligand D (1.74 g, 83%). $^1$H NMR (CDCl$_3$): δ 1.31 (s, C(CH$_3$)$_3$), 1.47 (s, C(CH$_3$)$_3$), 7.12–7.27 (m, Ar), 7.46 (d, Ar), 8.69 (s, CH). $^{19}$F NMR (CDCl$_3$): δ −6.11 (s). In a Schlenk tube under nitrogen, 0.8583 g (2.62 mmol) of Ligand D was dissolved in 20 mL of diethyl ether. The solution was cooled to −60° C. and 1.64 mL (2.62 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.143 mL, 1.31 mmol) in ether (15 mL) and toluene (4 mL) at −60° C. The reaction mixture was stirred at room temperature for 16 hours and the solvent was removed under vacuum. Residues were redisolved in methylene chloride and filtered through Celite. The solvent was removed once again, and the crude product was recrystallized in toluene/hexanes at −20° C. Red-brown crystals of Complex D were obtained (0.388 g, 39%). In solution, two diastereomers were present, with a C$_2$-symmetric species predominating over a C$_1$-symmetric isomer. $^1$H NMR (CDCl$_3$): δ 1.20 (s, C(CH$_3$)$_3$, C$_1$ isomer), 1.26 (s, C(CH$_3$)$_3$), 1.29 (s, C(CH$_3$)$_3$), 6.91 (m, Ar), 7.08 (d, Ar), 7.30–7.46 (m, Ar), 7.43 (d, Ar), 8.10 (s, CH), 8.34 (s, CH, C$_1$ isomer). $^{19}$F NMR (CDCl$_3$): δ 7.22 (d), 10.06 (d).

EXAMPLE V

Synthesis of Complex E

To a Schlenk tube were added 1.7436 g (13.5 mmol) of 2,6-difluoroaniline, 1.5824 g (6.75 mmol) of 3,5-di-tert-butylsalicylaldehyde, and 4 Å molecular sieves. The solution was heated at 120° C. for 18 hours. Crystallization from methanol at −20° C. produced Ligand E as a yellow crystalline solid (1.78 g, 76%). $^1$H NMR (CDCl$_3$): δ 1.33 (s, C(CH$_3$)$_3$), 1.45 (s, C(CH$_3$)$_3$), 6.94–7.05 (m, Ar), 7.06–7.14 (m, Ar), 7.18 (d, Ar), 7.47 (d, Ar), 8.84 (s, CH). $^{19}$F NMR (CDCl$_3$): δ 9.14 (t). In a Schlenk tube under nitrogen, 0.9584 g (2.77 mmol) of Ligand E was dissolved in 20 mL of diethyl ether. The solution was cooled to −60° C. and 1.64 mL (2.62 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.152 mL, 1.39 mmol) in ether (15 mL) and toluene (4 mL) at −60° C. The reaction mixture was stirred at room temperature for 16 hours and the solvent was removed under vacuum. Residues were redisolved in methylene chloride and filtered through Celite. The solvent was removed once again, and the crude product was recrystallized in toluene/hexanes. Red-brown crystals of Complex E were obtained (0.72 g, 64%). $^1$H NMR(CDCl$_3$): δ 1.26 (s, C(CH$_3$)$_3$), 1.30 (s, C(CH$_3$)$_3$), 6.43 (m, Ar), 6.87 (t, Ar), 6.95 (m, Ar), 7.15 (d, Ar), 7.51 (d, Ar), 8.19 (s, CH). $^{19}$F NMR (CDCl$_3$): δ 13.78 (s), 16.81 (s).

EXAMPLE VI

Synthesis of Complex F

N-sulfinyl-2,4,6-trifluoroaniline was prepared by refluxing 2,4,6-trifluoroaniline in thionyl chloride. Excess SOCl$_2$ was removed by distillation. To a Schlenk tube were added 25 mL of benzene, 1.386 g (5.91 mmol) 3,5-di-tert-butylsalicylaldehyde, and 1.15 g (5.91 mmol) of N-sulfinyl-2,4,6-trifluoroaniline. This mixture was refluxed under nitrogen for 10 hours. The sulfinyl becomes SO$_2$ and the driving force for the reaction is SO$_2$. Removal of the solvent and recrystallization in methanol produced Ligand F as a yellow crystalline solid (1.42 g, 66%). $^1$H NMR (CDCl$_3$): δ 1.31 (s, C(CH$_3$)$_3$), 1.45 (s, C(CH$_3$)$_3$), 6.72–6.80 (m, Ar), 7.16 (d, Ar), 7.47 (d, Ar), 8.81 (s, CH), 13.17 (s, OH). $^{19}$F NMR (CDCl$_3$): δ −12.63 (t), 8.72 (m). In a Schlenk tube under nitrogen, 0.8144 g (2.24 mmol) of Ligand F was dissolved in 20 mL of diethyl ether. The solution was cooled to −60° C. and 1.40 mL (2.24 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.123 mL, 1.12 mmol) in ether (15 mL) and toluene (4 mL) at −60° C. The reaction mixture was stirred at room temperature for 16 hours and the solvent was removed under vacuum. Residues were redisolved in methylene chloride and filtered through Celite. The solvent was removed once again, and the crude product was recrystallized in toluene/hexanes. Red-brown crystals of Complex F were obtained (0.756 g, 80%). $^1$H NMR (CDCl$_3$): δ 1.29 (s, C(CH$_3$)$_3$), 1.30 (s, C(CH$_3$)$_3$), 6.21 (m, Ar), 6.65 (m, Ar), 7.14 (d, Ar), 7.56 (d, Ar), 8.15 (s, CH). $^{19}$F NMR (CDCl$_3$): δ 58.18 (s), 59.78 (s), 62.63 (p).

EXAMPLE VII

Synthesis of Complex G

N-sulfinylpentafluoroaniline was synthesized by refluxing pentafluoroaniline in excess SOCl$_2$. N-sulfinylpentafluoroaniline (2.29 g, 10 mmol) was then added to 3,5-di-tert-butylsalicylaldehyde (2.34 g, 10 mmol) in 20 mL dry benzene under nitrogen, and this solution was heated to reflux for 12 h. Removal of solvent under vacuum gave a yellow solid that was crystallized from methanol at −20° C., providing ligand G as a yellow crystalline solid (2.65 g, 66.4%). $^1$H NMR (CDCl$_3$, 300 MHz) δ 8.79 (1H, s, CH), 7.52 (1H, d, J=2.4 Hz, ArH), 7.18 (1H, d, J=2.4 Hz, ArH), 1.45 (9H, s, C(CH$_3$)$_3$), 1.30 (9H, s, C(CH$_3$)$_3$), $^{19}$F NMR (CDCl$_3$, 400 MHz): δ −19.82 (2F, q, J=15 Hz), −26.51 (1F, t, J=21 Hz), −30.16 (2F, m). $^{13}$C NMR (CDCl$_3$, 100 MHz): δ 166.2, 154.9, 153.9, 150.5, 136.9, 133.5, 125.1, 123.5, 122.2, 114.4, 108.2, 31.4, 30.4, 27.7, 25.64. To a stirred solution of ligand G (0.858 g, 2.15 mmol) in diethyl ether (20 mL) at −60° C. was added nBuLi (1.34 mL, 1.6 M in hexanes, 2.15 mmol) dropwise using a gas-tight syringe. This solution was allowed to slowly warm to room temperature and stirred for an additional 4 h. This solution was then added dropwise via cannula to a solution of TiCl$_4$ (0.204 g, 1.07 mmol) in diethyl ether (16 mL) and toluene (4 mL) at −78° C. The resulting solution was allowed to warm naturally to room temperature and stirred an additional 16 h. After removal of solvent, the residue was taken up in toluene and the precipitated LiCl was removed by filtration over a Celite plug. Removal of solvent in vacuo gave a deep red powder that was crystallized from a mixture of toluene/hexane to give the desired complex G as a deep red crystalline solid (0.702 g, 71% yield). $^1$H NMR (CDCl$_3$, 400 MHz) δ 8.20 (2H, s, CH), 7.66 (2H, d, J=2.4 Hz, ArH), 7.20 (2H, d, J=2.4 Hz, ArH), 1.32 (18H, s, C(CH$_3$)$_3$), 1.30 (18H, s, C(CH$_3$)$_3$), $^{13}$C NMR (CDCl$_3$, 100 MHz) δ 198.7, 174.0, 160.9, 144.9, 138.2, 134.4, 130.0, 129.2, 128.4, 125.5, 123.6, 35.5, 34.7, 31.3, 29.5. Crystal data (solid state structure): orthorhombic, a=16.2248(7) Å b=23.7332(10) Å, c=24.9966(11) Å, α=β=γ=90°, V=9625.4(7) Å$^3$, space group Pbca; Z=8 formula weight=993.68 for C$_{42}$H$_{42}$Cl$_2$F$_{10}$N$_2$O$_2$Ti.C$_6$H$_6$, and density (calc.)=1.371 g/cm$^3$; R(F)=0.047 and R$_w$(F)=0.114 (I>2σ(I)).

EXAMPLE VIII

Synthesis of Complex H

To a Schlenk tube were added 0.9259 g (7.17 mmol) of 3,5-difluoroaniline, 1.6806 g (7.17 mmol) of 3,5-di-tert-butylsalicylaldehyde, and 4 Å molecular sieves. The solution was heated at 120° C. for 18 hours. Crystallization from methanol at −20° C. produced Ligand H as a brown crystalline solid (1.99 g, 80%). $^1$H NMR (CDCl$_3$): δ 1.31 (s, C(CH$_3$)$_3$), 1.46 (s, C(CH$_3$)$_3$), 6.68–6.73 (m, Ar), 6.79–6.82 (m, Ar), 7.22 (d, Ar), 7.48 (d, Ar), 8.60 (s, CH), 13.14 (s, OH). $^{19}$F NMR (CDCl$_3$): δ −23.40 (t). In a Schlenk tube under nitrogen, 1.1386 g (3.29 mmol) of Ligand H was dissolved in 20 mL of diethyl ether. The solution was cooled to −60° C. and 2.06 mL (3.29 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.181 mL, 1.65 mmol) in ether (15 mL) and toluene (4 mL) at −60° C. The reaction mixture was stirred at room temperature for 16 hours and the solvent was removed under vacuum. Residues were redissolved in methylene chloride and filtered through Celite. The solvent was removed once again, and the crude product was recrystallized in toluene/hexanes. Red-brown crystals of Complex H were obtained (0.74 g, 55%). In solution, two diastereomers were present, with a C$_2$-symmetric species predominating over a C$_1$-symmetric isomer. $^1$H NMR (CDCl$_3$): δ 1.26 (s, C(CH$_3$)$_3$), 1.29 (s, C(CH$_3$)$_3$), C$_1$ isomer), 1.30 (s, C(CH$_3$)$_3$, C$_1$ isomer), 1.36 (s, C(CH$_3$)$_3$), 6.29 (m, Ar), 6.42 (m, Ar), 6.53 (m, Ar), 6.64–6.69 (m, Ar, C$_1$ isomer), 6.73–6.77 (m, Ar, C$_1$ isomer), 7.11 (d, Ar), 7.15 (m, Ar, C$_1$ isomer), 7.53 (d, Ar), 7.62 (d, Ar, C$_1$ isomer), 7.68 (d, Ar, C$_1$ isomer), 7.99 (s, CH, C$_1$ isomer), 8.03 (s, CH, C$_1$ isomer), 8.08 (s, CH). $^{19}$F NMR (CDCl$_3$): δ 22.94 (s), 23.96 (s), 24.99 (t).

EXAMPLE IX

Synthesis of Complex I

To a 250-mL Schlenk tube were added 20 mL of methanol, 1.7823 g (10 mmol) of 3-tert-butylsalicylaldehyde, and 0.93 g (10 mmol) of aniline. The solution was heated under reflux for 10 hours, followed by reduction of the solvent volume under vacuum. Crystallization at −20° C. afforded orange-yellow crystals of Ligand I (2.23 g, 88%). $^1$H NMR (CDCl$_3$): δ 1.45 (s, C(CH$_3$)$_3$), 6.80 (t, Ar), 7.12 (m, Ar), 7.40 (m, Ar), 8.60 (s, CH). In a Schlenk tube under nitrogen, 1.013 g (4 mmol) of Ligand I was dissolved in 20 mL of diethyl ether. The solution was cooled to −60° C. and 2.5 mL (4 mmol) of n-butyllithium (1.6 M in hexane) was added dropwise via gastight syringe. After warming to room temperature, stirring was continued for 4 hours. This solution was added dropwise via cannula to a second Schlenk tube containing a solution of TiCl$_4$ (0.219 mL, 2 mmol) in ether (15 mL) and toluene (4 mL) at −60° C. The reaction mixture was stirred at room temperature for 16 hours and the solvent was removed under vacuum. Residues were redissolved in methylene chloride and filtered through Celite. The solvent was removed once again, and the crude product was recrystallized in benzene/hexanes at −20° C. Red-brown crystals of Complex I were obtained (1.08 g, 78%). In solution, two diastereomers were present, with a C$_2$-symmetric species predominating over a C$_1$-symmetric isomer. $^1$H NMR (CDCl$_3$): δ 1.34 (s, C(CH$_3$)$_3$), 6.74–6.84 (m, Ar), 6.98–7.30 (m, Ar), 7.40–7.43 (m, Ar), 7.54–7.63 (m, Ar), 7.91 (s, CH, C$_1$ isomer), 8.04 (s, CH, C$_1$ isomer), 8.06 (s, CH).

EXAMPLE X

Preparation of Syndiotactic Polypropylene and of Block Copolymers Containing Syndiotactic Polypropylene Blocks The following general procedure was used for preparation of syndiotactic polypropylene: A 6 oz Lab-Crest® pressure reaction vessel (Andrews Glass) equipped with a magnetic stir bar was first conditioned under dynamic vacuum (20 mTorr) and high temperature (200° C.) and then charged with a desired amount of PMAO and toluene (150 mL). The reactor was the equilibrated at 0° C. in an ice bath. At this point, the reactor atmosphere was exchanged with propylene gas three times, and then the solution was saturated with propylene under pressure (40 psi). The required amount of the titanium catalyst was dissolved in toluene (8 mL) at RT under nitrogen, and the solution was added to the reactor via gas-tight syringe to initiate the polymerization. After the desired period of time, the reactor was vented. The polymer was precipitated in copious methanol/HCl, filtered, washed with methanol, and then dried in vacuo to constant weight.

The following procedure was used for preparation of syndio-propylene-block-poly(ethylene-co-propylene): A 6 oz Lab-Crest® pressure reaction vessel (Andrews Glass) equipped with a magnetic stir bar was first conditioned under dynamic vacuum (20 mTorr) and high temperature (200° C.) and then charged with PMAO (15 mmol) and toluene (150 mL). The reactor was cooled to 0° C., and the atmosphere was exchanged with propylene gas three times, and then saturated with propylene under pressure (40 psi). A solution of titanium complex (0.10 mmol) in toluene (6 mL) was then added to the reactor via gas-tight syringe to initiate the polymerization. After the initial propylene polymerization, a 5-mL sample was removed via gas-tight syringe, and ethylene at 5 psi overpressure was introduced into the reactor. After 1 hour of additional polymerization time, the reaction was quenched by injection of methanol/HCl (2 mL, 10% vol HCl). After venting the reactor, the polymer was precipitated in copious methanol/HCl, filtered, washed with methanol, and then dried in vacuo to constant weight.

The following general procedure was used for preparation of syndio-polypropylene-block-poly(ethylene-co-propylene)-block-syndio-propylene: A 6 oz Lab-Crest® pressure reaction vessel (Andrews Glass) equipped with a magnetic stir bar was first conditioned under dynamic vacuum (20 mTorr) and high temperature (200° C.) and then charged with PMAO (15 mmol) and toluene (150 mL). The reactor was cooled to 0° C., and the atmosphere was exchanged with propylene gas three times, and then saturated with propylene under pressure (40 psi). A solution of titanium complex (0.10 mmol) in toluene (6 mL) was then added to the reactor via gas-tight syringe to initiate the polymerization. After the initial propylene polymerization, a 5-mL sample was removed via gas-tight syringe, and ethylene at 5 psi overpressure was introduced into the reactor. After the reaction times as stated in Table II hereinafter of additional polymerization time, a sample was removed for analysis and the ethylene source was shut off. The reaction quickly consumed the residual ethylene and reverted to propylene polymerization for the desired amount of time. Then the reaction was quenched by injection of methanol/HCl (2 mL, 10% vol HCl). After venting the reactor, the polymer was precipitated in copious methanol 10% HCl, filtered, washed with methanol, and then dried in vacuo to constant weight.

Other reaction conditions and results are given in Table II below and in the footnotes thereto. In Table II, "rxn" means reaction, P means propylene, and E means ethylene. The MAO used was PMAO.

TABLE II[a]

| Complex | Rxn time (h) | $T_{rxn}$ (° C.) | Monomer | Yield (g) | Activity[b] | $M_n^c$ | $M_w/M_n^c$ | [rrrr] |
|---|---|---|---|---|---|---|---|---|
| A | 24 | 0 | P | 4.20 | 1.75 | 9,910 | 2.14 | 0.78 |
| B | 24 | 0 | P | 3.62 | 1.51 | 16,943 | 1.44 | 0.87 |
| C | 24 | 0 | P | 3.70 | 1.54 | 8,850 | 1.59 | 0.73 |
| D | 24 | 0 | P | 0.38 | 0.16 | 3,010 | 1.07 | 0.52 |
| E | 24 | 0 | P | 0.56 | 0.23 | 15,487 | 1.06 | 0.83 |
| F | 24 | 0 | P | 2.48 | 1.03 | 40,208 | 1.08 | 0.95 |
| G | 0.25 | 0 | P | 0.49 | 19.6 | 11,100 | 1.09 | 0.96 |
| G | 0.50 | 0 | P | 0.97 | 19.4 | 24,500 | 1.08 | 0.96 |
| G | 1.5 | 0 | P | 1.79 | 11.9 | 44,700 | 1.11 | 0.96 |
| G | 3.1 | 0 | P | 3.84 | 12.4 | 75,800 | 1.08 | 0.96 |
| G | 5.2 | 0 | P | 5.34 | 10.3 | 95,900 | 1.11 | 0.96 |
| G | 66[d] | 0 | P | 14.2 | 2.15 | 307,700 | 1.34 | 0.96 |
| G | 24 | 20 | P | 7.43 | 3.09 | 102,500[e] | 1.13[e] | 0.96 |
| H | 24 | 0 | P | 23.4 | 9.75 | 13,584 | 1.91 | 0.81 |
| I | 24 | 0 | P | 3.00 | 1.25 | 5,000 | 2.59 | 0.79 |
| G | 2.0/1.0[f] | 0 | P/E | 11.2 | NA | 38,400/ 145,100[g] | 1.11/ 1.12[g] | 0.96 |
| G | 2.0/0.33/ 2.0[h] | 0 | P/E/P | NA | NA | 30,900/ 44,200/ 70,300[i] | 1.07/ 1.08/ 1.08[i] | 0.96[l] |
| G | 2.0/1.0/ 2.0[j] | 0 | P/E/P | NA | NA | 38,000/ 169,000[i] | 1.06/ 1.09/ | 0.96[l] |
| G | 2.0/0.50/ 3.0[k] | 0 | P/E/P | NA | NA | 36,000/ 217,000/ 260,000[i] | 1.11/ 1.11/ 1.18[i] | 0.96[l] |

[a]General conditions: Complex (0.1 mmol) in toluene (6 ml) added to a propylene saturated (40 psi) MAO solution (150 ml toluene; [Al]/[Ti] = 150).
[b]kg PP/(mol Ti · h).
[c]Determined by GPC in 1,2,4-trichlorobenzene at 140° C. versus polystyrene standards.
[d]0.04 mmol Ti and 6 mmol MAO in 150 mL toluene.
[e]GPC versus PP standards.
[f]After reaction with propylene (40 psi) for 2 hours, a 1–10 psi overpressure of ethylene was added for 1 hour.
[g]Data for the initial polypropylene block and the final poly(propylene)-block-poly(ethylene-co-propylene) diblock polymer.
[h]After reaction with propylene (40 psi) for 2 hours, a 1–10 psi overpressure of ethylene was added for 20 minutes; once ethylene flow was terminated the ethylene was consumed and the reaction was allowed to return to propylene homopolymerization for 2 hours.
[i]Data for the initial polypropylene block, the poly(propylene)-block-poly(ethylene-co-propylene) diblock polymer, and the final poly(propylene)-block-poly(ethylene-co-propylene)-block-poly(propylene) triblock polymer.
[j]After reaction with propylene (40 psi) for 2 hours, a 1–10 psi overpressure of ethylene was added for 1 hour; once ethylene flow was terminated the ethylene was consumed and the reaction was allowed to return to propylene homopolymerization for 2 hours.
[k]After reaction with propylene (30 psi) for 2 hours, a 1–10 psi overpressure of ethylene was added for 30 minutes; once ethylene flow was terminated the ethylene was consumed and the reaction was allowed to return to propylene homopolymerization for 3 hours.
[l]All of these polymers have elastomeric properties except in the first triblock run (run 17 in Table II), the polypropylene blocks give a stiff characteristic.

In Table II, the first 15 entries represent preparation of syndiotactic polypropylene, the sixteenth entry represents preparation of SPP-EP diblock and the seventeenth, eighteenth and nineteenth entries represent preparation of SPP-EP-SPP triblock. The entries in Table II where complexes A, H and I were used provide olefin terminated product. The product for the entry for Complex H has the formula (II) where n=323.

SPP-EP-SPP-EP-SPP pentablock is formed when the procedure of footnote k to Table II is modified to propylene homopolymerization for the third block to 2 hours whereupon a 5 psi overpressure of ethylene is added for 30 minutes whereupon ethylene flow is terminated and reaction is allowed to return to propylene homopolymerization for 2 hours.

Poly(propylene)-block-poly(1-butene-co-propylene) diblock polymer is formed when the procedure for note f to Table II, is modified to substitute an overpressure of 1-butene for 1 hour for the overpressure of ethylene.

EXAMPLE XI

The following procedure is used for the preparation of syndiotactic poly(1-butene). A 6 oz Lab-Crest® pressure vessel (Andrews Glass) equipped with a magnetic stir bar is first conditioned under dynamic vacuum and high temperature and then charged with 15 mmol PMAO and toluene (150 ml). The reactor is equilibrated at 0° C. in an ice bath. At this point, 10 ml of 1-butene is added. Then 0.1 mmol complex G is dissolved in toluene (8 ml) at RT under nitrogen, and the solution is added to the reactor via gas-tight syringe to initiate the polymerization. After 12 hours, the reactor is vented. The polymer is precipitated in copious methanol/HCl, filtered, washed with methanol and dried in vacuo to constant weight. The poly(1-butene) product has $M_n$ of about 60,000, $M_w/M_n$ of about 1.15 and [rrrr] of about 0.95.

Variations

Many variation will be obvious to those skied in the art. Therefore, the invention is defined by the claims.

What is claimed is:

1. Block copolymer having $M_w$ ranging from 10,000 to 500,000 comprising at least one block of syndiotactic polypropylene and at least one block of poly(ethylene/propylene) where the ethylene content ranges from 1 to 100% by weight, containing a volume fraction of syndiotactic polypropylene ranges from 0.20 to 0.99 where said at least one block of syndiotactic polypropylene has $M_w/M_n$ ranging from 1.05 to 1.35 and [rrrr] pentad content of at least 0.80.

2. Block copolymer having $M_w$ ranging from 10,000 to 500,000 comprising at least one block of syndiotactic polypropylene and at least one block of poly(ethylene/propylene) where the ethylene content ranges from 1 to 100% by weight, containing a volume fraction of syndiotactic polypropylene ranges from 0.20 to 0.99, where said at least one block of syndiotactic polypropylene has [rrrr] pentad content of at least 0.95.

3. The block copolymer of claim 1 consisting essentially of one block of syndiotactic polypropylene and one block of poly(ethylene-co-propylene) where the volume fraction of syndiotactic polypropylene ranges from 0.20 to 0.99.

4. The block copolymer of claim 1 consisting essentially of a block of syndiotactic polypropylene followed by a block of poly(ethylene-co-propylene) followed by a block of syndiotactic polypropylene, where the volume fraction of syndiotactic polypropylene ranges from 0.20 to 0.99.

5. Block copolymer having $M_w$ ranging from 10,000 to 500,000 consisting essentially of a block of syndiotactic polypropylene followed by a block of poly(ethylene-co-propylene) where the ethylene content ranges from 1 to 100% by weight, followed by a block of syndiotactic polypropylene followed by a block of poly(ethylene-co-propylene) where the ethylene content ranges from 1 to 100% by weight followed by a block of syndiotactic polypropylene, where the volume fraction of syndiotactic polypropylene ranges from 0.20 to 0.99.

6. Block copolymer having $M_w$ ranging from 10,000 to 500,000 comprising at least one block of syndiotactic polypropylene and at least one block of poly(1-butene/propylene) where the 1-butene content ranges from 1 to 100% by weight, containing a volume fraction of syndiotactic polypropylene ranges from 0.20 to 0.99, where said at least one block of syndiotactic polypropylene has [rrrr] pentad content of at least ranging from 0.80.

7. The block copolymer of claim 6 where said at least one block of syndiotactic polypropylene has [rrrr] pentad content of at least 0.95.

* * * * *

UNITED STATES PATENT AND TRADEMARK OFFICE
CERTIFICATE OF CORRECTION

PATENT NO.         : 6,787,624 B2
APPLICATION NO. : 10/386694
DATED                  : September 7, 2004
INVENTOR(S)       : Geoffrey W. Coates et al.

It is certified that error appears in the above-identified patent and that said Letters Patent is hereby corrected as shown below:

Claim 1 (column 19, line 35), change "ranges" to --ranging--.

Claim 2 (column 20, line 4), change "ranges" to --ranging--.

Claim 6 (column 20, line 33), change "ranges" to --ranging--.

Claim 6 (column 20, line 35), change "at least ranging from 0.80" to --at least 0.80--.

Signed and Sealed this

Eighth Day of January, 2008

JON W. DUDAS
*Director of the United States Patent and Trademark Office*

UNITED STATES PATENT AND TRADEMARK OFFICE
CERTIFICATE OF CORRECTION

PATENT NO.       : 6,787,624 B2
APPLICATION NO.  : 10/386694
DATED            : September 7, 2004
INVENTOR(S)      : Geoffrey W. Coates et al.

It is certified that error appears in the above-identified patent and that said Letters Patent is hereby corrected as shown below:

Claim 1 (column 19, line 35), change "ranges" to --ranging--.

Claim 2 (column 20, line 4), change "ranges" to --ranging--.

Claim 6 (column 20, line 33), change "ranges" to --ranging--.

Claim 6 (column 20, line 35), change "at least ranging from 0.80" to --at least 0.80--.

Signed and Sealed this

Twenty-ninth Day of January, 2008

JON W. DUDAS
*Director of the United States Patent and Trademark Office*